United States Patent [19]

Otani

[11] Patent Number: 5,188,115
[45] Date of Patent: Feb. 23, 1993

[54] RATCHETING MECHANISM FOR TIGHTENING CUFF OR BLOOD PRESSURE MONITOR

[75] Inventor: Haruhide Otani, Matsusaka, Japan

[73] Assignee: Omron Corporation, Kyoto, Japan

[21] Appl. No.: 639,860

[22] Filed: Jan. 11, 1991

[30] Foreign Application Priority Data

Jan. 11, 1990 [JP] Japan .................................. 2-5299
Jun. 19, 1990 [JP] Japan ................................ 2-160726

[51] Int. Cl.⁵ .............................................. A61B 5/022
[52] U.S. Cl. .................................. 128/677; 128/686; 74/501.05 R; 74/502; 74/422
[58] Field of Search ............... 128/686, 677; 606/203; 74/501.5, 500.5, 502, 503, 422, 110, 109

[56] References Cited

U.S. PATENT DOCUMENTS

2,714,379  8/1955  Raines et al. .
4,308,871  5/1982  Shouda et al. .
4,850,369  7/1989  Yamasawa .
5,107,848  4/1992  Oku .................................... 128/686

FOREIGN PATENT DOCUMENTS

1466900  8/1964  Fed. Rep. of Germany .

*Primary Examiner*—Lee S. Cohen
*Assistant Examiner*—Brian L. Casler
*Attorney, Agent, or Firm*—Fish & Richardson

[57] ABSTRACT

A ratcheting device for use in tightening the cuff of a blood pressure monitor has a lever, a lever mounting which is attached to one end of the cuff and which holds the lever so that it can be moved in a given direction or an opposite direction. An elastic body is disposed between the lever and the lever mounting to transmit a force applied to the lever into the lever mounting by elastic deformation of the elastic body. Interdental spaces are formed between saw teeth on the inner surface of a cam and extend in the given and opposite directions in which the lever moves. A ratchet having pawls thereon which can engage with the interdental spaces is provided; this rachet is immobilized by the engagement of the pawls in the interdental spaces when the pressure applied to the lever exceeds a given value.

6 Claims, 12 Drawing Sheets

RATCHETING MECHANISM FOR TIGHTENING CUFF OR BLOOD PRESSURE MONITOR

FIELD OF THE INVENTION

This invention relates to a ratcheting device which can be used in the wrapping mechanism of a cuff on a blood pressure monitor of the type which measures blood pressure by obstructing the flow of blood in a finger artery.

BACKGROUND OF THE INVENTION

Figure 12:
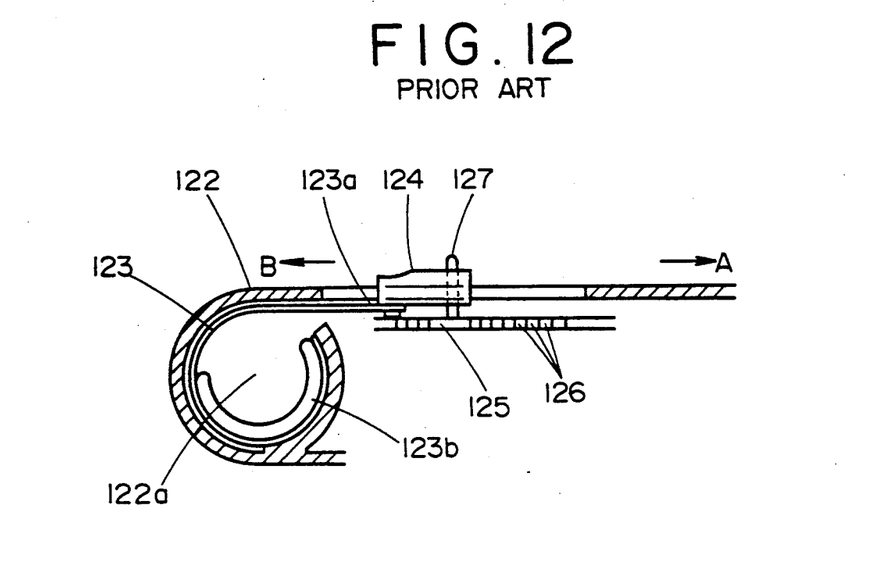
FIG. 12 shows a cross sectional view of a cuff winding mechanism used in existing blood pressure monitors.
Figure 13:
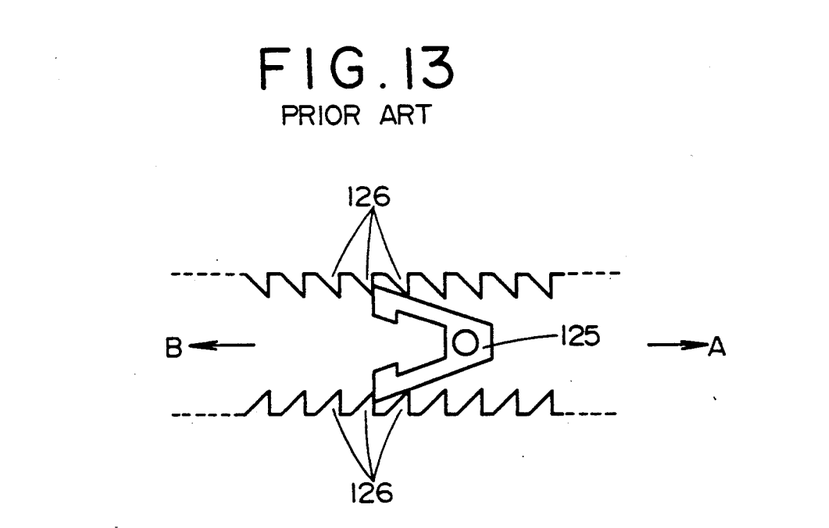
FIG. 13 illustrates the interdental spaces and pawls in the cuff winding mechanism depicted in FIG. 12.

To facilitate the wrapping of the cuff onto the finger, prior blood pressure monitors used on a finger employ the cuff wrapping mechanism shown in FIGS. 12 and 13. In FIG. 12, 122 is the case, and 123 is the cuff within the case. Rubber chamber 123b is attached to cuff 123.

The protruding end 123a of cuff 123 is fixed to lever 124. This lever is installed on case 122 in such a way that it can slide both in direction A, which tightens the cuff, and in direction B, which loosens the cuff. An elastic pawl 125 is provided on lever 124. As shown in FIG. 13, pawl 125 engages interdental spaces 126, which are located in two parallel rows along the path of movement of lever 124. Thus, the pawl prevents the lever from moving in direction B and loosening the cuff.

To measure a person's blood pressure, the person inserts a finger, usually the index finger, into opening 122a in case 122. Lever 124 is then moved in direction A to tighten the cuff. During tightening, pawl 125 is elastically deformed and passes over interdental spaces 126. When the appropriate cuff pressure has been attained, the operator releases lever 124, and pawl 125 engages in interdental spaces 126. This fixes the position of lever 124 and keeps cuff 123 wrapped around the patient's finger. Air is then pumped into rubber chamber 123b until the flow of blood in the finger artery is obstructed, and the blood pressure is measured.

When the blood pressure measurement has been completed, button 127 is pressed, causing pawl 125 to move down so that it is released from interdental spaces 126. Lever 124 slides in direction B, allowing cuff 123 to loosen.

With the existing cuff wrapping mechanism described above, the operator has a tendency to apply great force to lever 124 at the moment pawl 125 is slipping past teeth 126. This causes the pressure with which the cuff is wrapped to vary. For this reason, the tightness of the cuff is variable, and there is a pronounced tendency to overtighten it.

If cuff 123 is not wrapped sufficiently tightly, the volume of rubber chamber 123b will be increased, which will cause it to take longer for the cuff to be pressurized. Further, the area of the surface of rubber chamber 123b which contacts the finger will be decreased, which increases the chance that the rubber will wrinkle. If this happens, the blood pressure will not be measured correctly. Problems such as these are well known in blood pressure monitors employing the oscillation technique, in which the change in air pressure inside rubber chamber 123b is used to detect the pulse wave.

In contrast, if cuff 123 is wrapped too tightly, the blood in the finger can be completely obstructed, which will cause pain to the patient. To prevent cuff 123 from being wrapped too tightly, one could conceivably use deeper teeth for the toothed portions of 126, but this would cause the tightness to vary even more, and the operating noise would become much louder.

SUMMARY OF THE INVENTION

In view of the above problems, the purpose of this invention is to provide a ratcheting device which, when used in a blood pressure monitor, will allow the cuff easily to be wrapped to the appropriate tightness while minimizing operating noise.

The ratcheting device with which this invention is concerned includes a mounting for a lever which can be moved in a given direction or its opposite as the cuff is to be tightened or loosened. A lever which is capable of moving in the given direction or its opposite is installed on the mounting. An elastic body is situated between this lever and its mounting which can transmit the force applied to the lever into the lever mounting by elastic deformation. There is a ratchet with pawls and interdental spaces provided along the two directions in which the lever moves into which the pawls can fall. Finally, there is a means for immobilizing the ratchet, so that the pawls engage in the interdental spaces when the pressure applied to the lever exceeds a given value. With this design, the lever mounting can move smoothly until the pawls of the ratchet engage in the interdental spaces, thus minimizing the operating noise of the lever mounting.

In operation, the lever mounting runs into a stop, and the elastic body is compressed. When the compressive force exceeds a given value, the means for immobilizing the lever cause the pawls to engage in the interdental spaces. The lever mounting can move no further in the given direction, even if additional force is applied in that direction. Thus, it is impossible to apply excessive force to the person's finger.

DETAILED DESCRIPTION OF THE INVENTION

We shall now explain an embodiment of this invention with reference to FIGS. 1 through 6, starting with a summary of how the invention works in this embodiment.

Figure 1A:
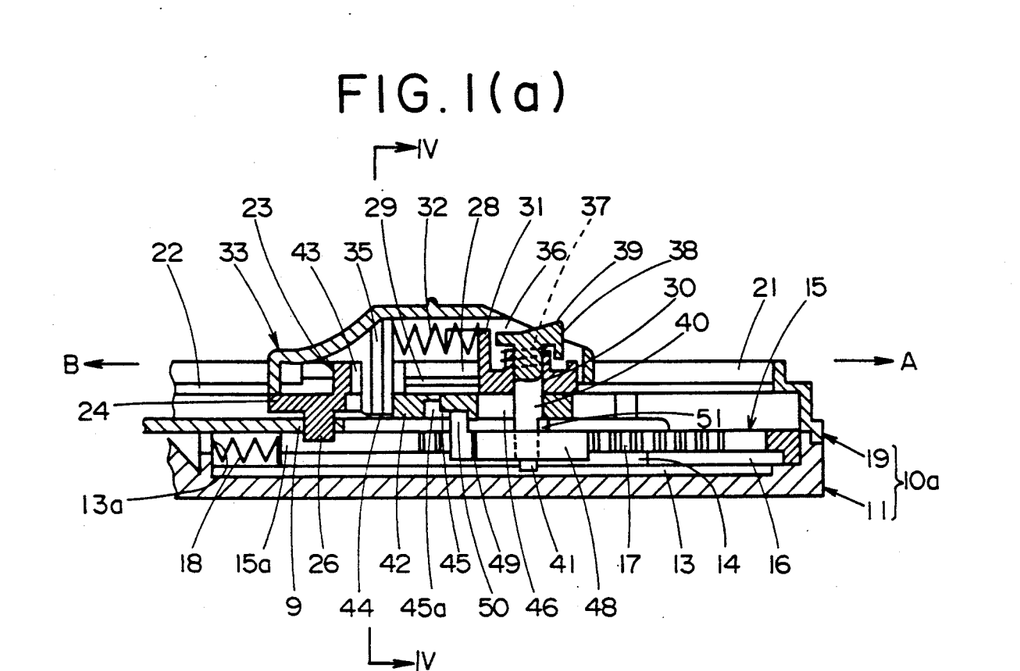
FIG. 1(a) is a cross sectional view of the cuff tightening unit of an embodiment of this invention, shown with the cuff loosened.
Figure 4:
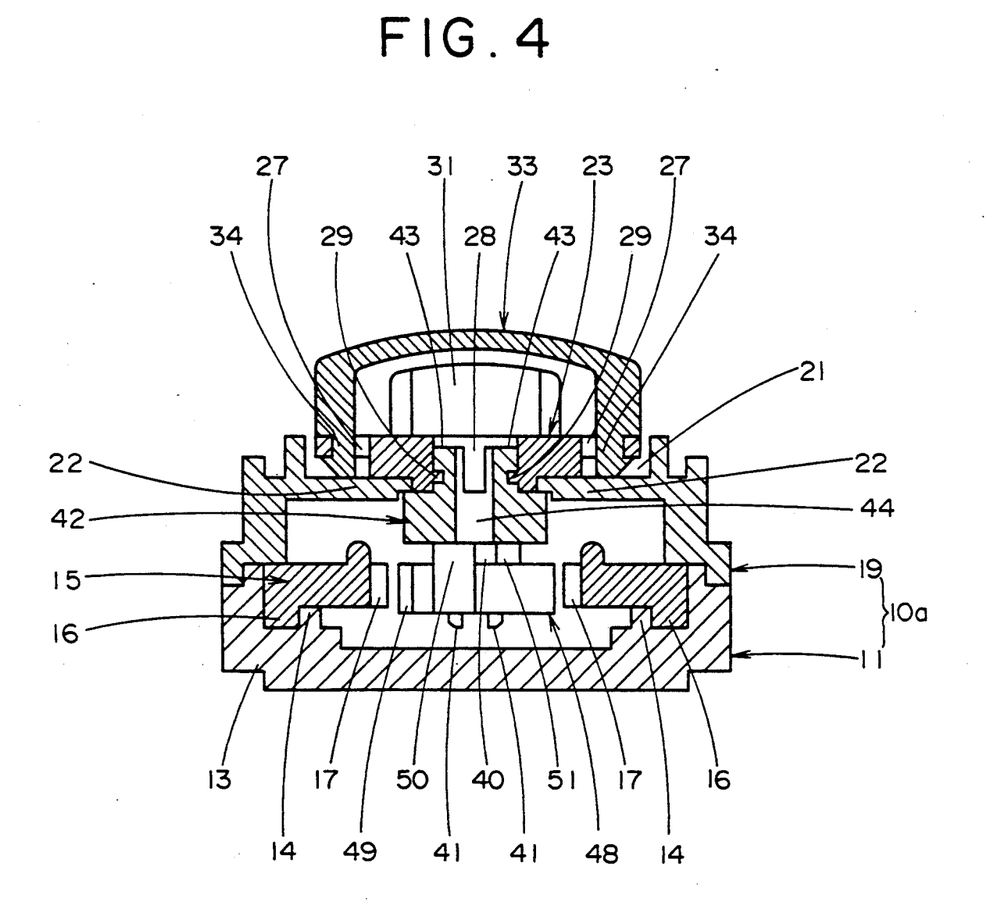
FIG. 4 is an enlarged view of the cross section taken along line IV—IV in FIG. 1(a).
Figure 5:
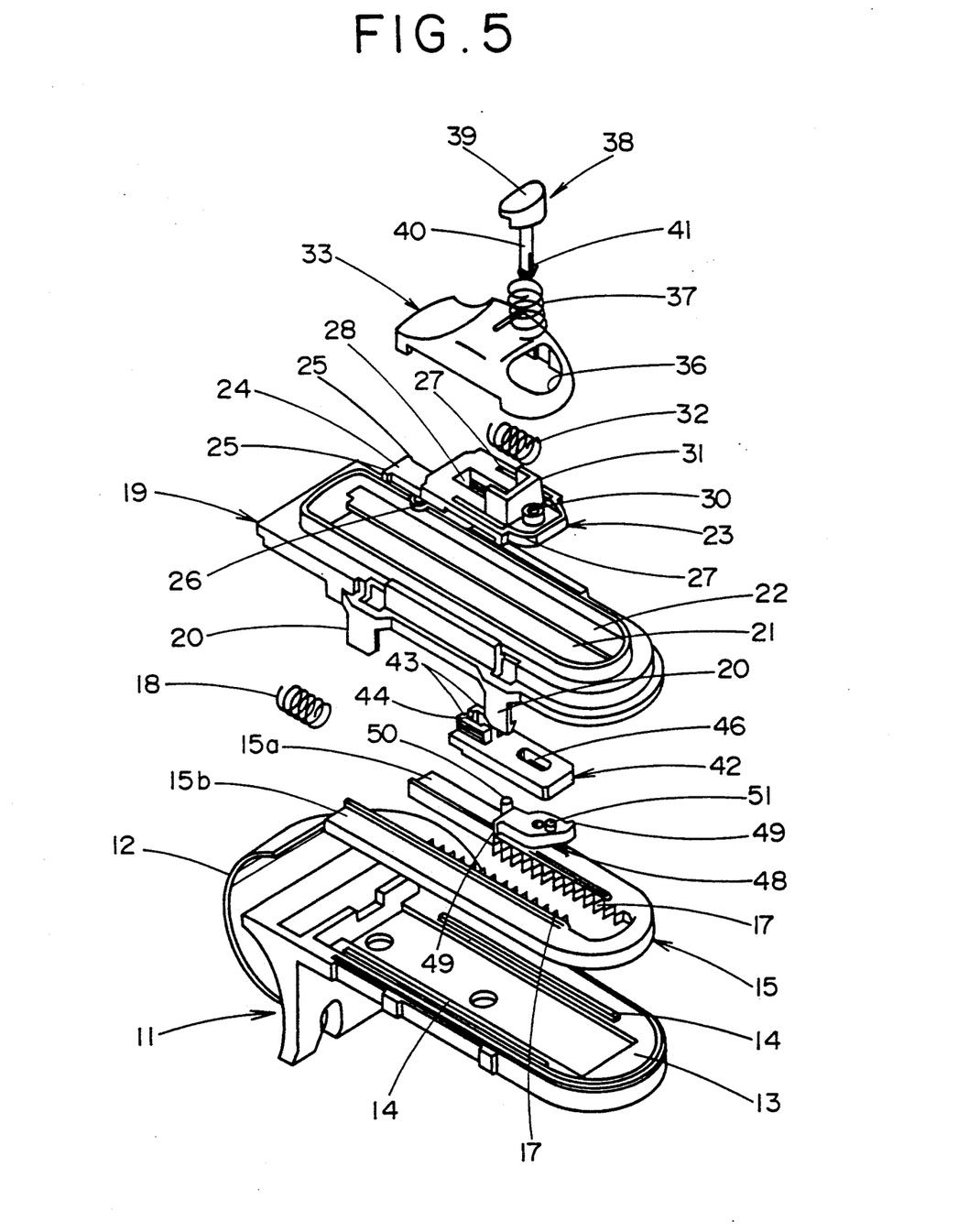
FIG. 5 is an oblique exploded view of the disassembled parts of the cuff tightening unit of FIG. 1(a).
Figure 6:
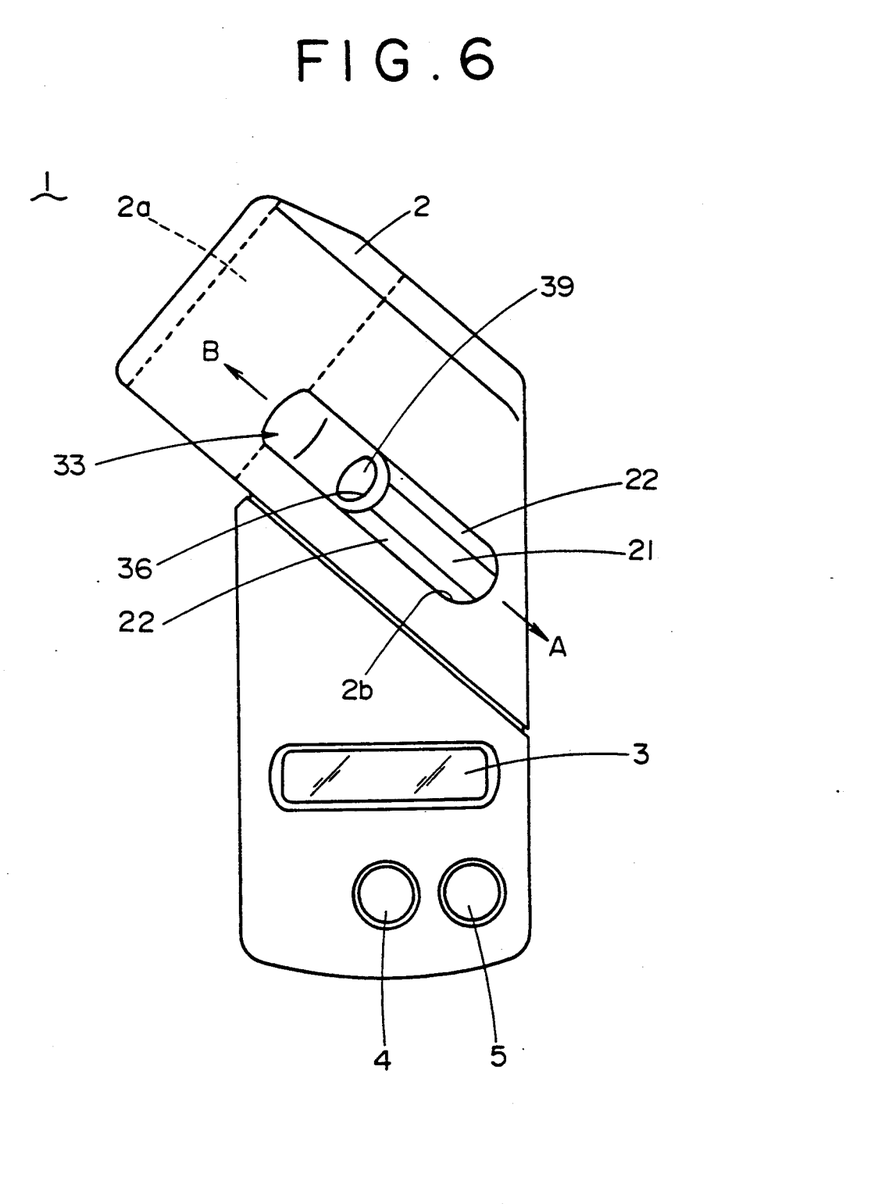
FIG. 6 is a frontal view of the exterior of the finger cuff-type electronic blood pressure monitor in which a cuff tightening unit of the type depicted in FIG. 1(a) is installed.

In FIG. 6, finger-cuff electronic blood pressure monitor 1 has a liquid crystal display 3, which displays blood pressure values and other information, and operating buttons 4 and 5 are located on case 2, which encloses blood pressure monitor 1. The cuff tightening unit 10, as depicted in FIGS. 1(a) and (b), FIG. 4 and FIG. 5, is attached to case 2. A finger can be inserted into part 2a. Slot 2b, in which the lever slides, is also provided.

Figure 1B:
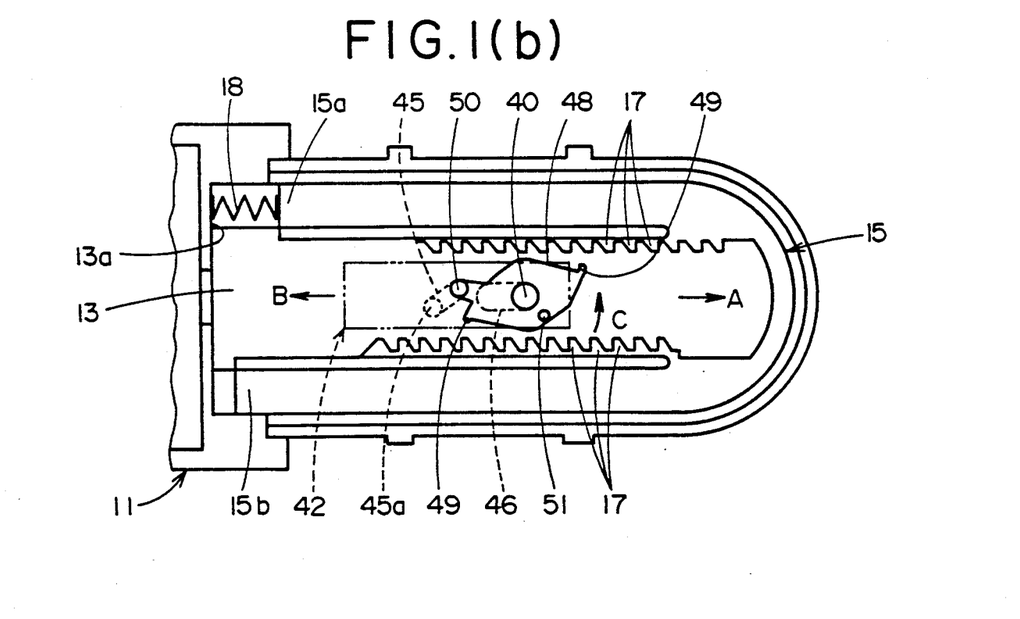
FIG. 1(b) shows the cuff tightening unit of FIG. 1(a), illustrating the relationship between the ratchet and cam when the cuff is loosened.

FIG. 1(a) is a cross sectional view of cuff tightening unit 10 when the cuff is loose. FIG. 1(b) illustrates the relationship between cam 15 and ratchet 48 by showing an overhead view of cuff tightening unit 10 with cover 19 removed. FIGS. 2(b) and 3(b) show the same view. FIG. 4 shows an enlarged cross section along the area in FIG. 1(a) indicated by line IV—IV. FIG. 5 shows an oblique exploded view of the disassembled components of cuff-tightening unit 10. With its housing 10a removed, cuff-tightening unit 10 includes base 11 and cover 19, cam 15, lever mounting 23, lever 33, stop 42, ratchet 48 and coil springs 18, 32 and 37 as its major components. For the sake of convenience and simplicity, the unit is broken down vertically in the following explanation.

The ratcheting device of this invention includes a mounting 23 for a lever which can be moved in a given direction (A) or its opposite (B). A lever 33, capable of moving in either direction (A) or (B), is installed on mounting 23. An elastic body 32 is situated between lever 33 and its mounting 23 which can transmit the force applied to the lever into the lever mounting by elastically deforming. A ratchet 48 is provided with pawls 49 which can fall into interdental spaces 17 provided along the two directions (A) and (B) in which the lever moves. The means for immobilizing the ratchet is depicted by reference numerals 45, 50; this means causes the pawls 49 to engage in the interdental spaces 17 when the pressure applied to the lever 33 exceeds a given value.

In this embodiment of the invention, when the lever 33 is moved in direction (A), the force is transmitted through the elastic body 32 to the lever mounting 23, which also moves in direction (A). When the lever has reached a certain point, the lever mounting 23 is stopped, and the elastic body 32 is compressed. When the compressive force exceeds a given value, the means for immobilizing the lever 45, 50 causes the pawls 49 to engage in the interdental spaces 17, thus securing the ratchet. As a result, the lever mounting 23 is locked into its position and can move no further in direction (A), even if more force is applied to the lever. Therefore it is not possible to apply an excessive force to the finger disposed in the cuff because of this arrangement. When this ratcheting device is employed in a blood pressure monitor, it prevents overtightening of the cuff. Also, because the lever mounting moves smoothly until the pawls of the ratchet engage in the interdental spaces, operating noise is kept to a minimum.

Base 11 as shown in FIG. 5 includes cylindrical cuff sleeve 12 and cam sleeve 13, which form a single unit. Inside cam sleeve 13 is U-shaped cam 15. This cam is constructed in such a way that it can slide a certain distance within cam sleeve 13 in either direction (A), which tightens the cuff, or direction (B), which loosens the cuff. Guide rails 14 are provided on the inner surface of cam sleeve 13. As shown in FIG. 4, these guide rails 14 contact corresponding ridges 16 on the underside of cam 15 in order to guide it so that it can move smoothly.

The inside of cam 15 has parallel rows of sawteeth defining interdental spaces 17. One end of the cam, 15a, is slightly shorter than the other end, 15b. Coil spring 18 is interposed between cam end 15a and vertical wall 13a of the cam sleeve so that it can absorb the force when cam 15 slides in direction (A) to tighten the cuff. Cam sleeve 13 is enclosed by cover 19, and is constructed in such a way that cam 15 and coil spring 18 cannot slip out of the sleeve. As shown in FIGS. 4 and 5, cover 19 is fastened to the cam sleeve by tabs 20, which engage on the bottom of cam sleeve 13 to secure the cover. Cover 19 has a long slot in it, slot 21, into which tabs 22 are inserted.

Lever mounting 23 is seated on tabs 22. The end 24 of lever mounting 23 protrudes downward between tabs 22. This end 24 has projections 25 on either side to prevent it from coming out of the tabs, and it also has an anchor pin, 26. This pin is anchored to the protruding end 9 of the cuff, which extends out of cuff cover 12. Lever 33 is mounted on lever mounting 23 in such a way that it can slide in direction (A) to tighten the cuff or in direction (B) to loosen the cuff. Tabs 34 on lever 33 are engaged, respectively, in slots 27 on lever mounting 23. These tabs serve to guide lever 33 in directions (A) and (B).

Pin 35 depends vertically from lever 33, passes through guide track 28 on lever mounting 23, and protrudes downward, as shown in FIG. 1(a). Coil spring 32 is interposed between spring pressure plate 31 on lever mounting 23 and the base of pin 35.

Button 38 is mounted on lever mounting 23. Button shaft 40 protrudes downward through hole 30 in lever mounting 23. Lever 33 has an opening 36 in it so that the head 39 of button 38 will not contact it. Coil spring 37 is attached to button shaft 40 and provides force in an upward direction.

As shown in FIGS. 1(a), 4 and 5, stop 42 is mounted to the bottom surface of lever mounting 23 in such a way that it, too, can slide in directions A and B. On the top surface of stop 42 there are two guide teeth 43, which fit into guide track 28 on lever mounting 23. These teeth engage, respectively, with guide rails 29. The lower end of the pin 35 inserts into hole 44 on stop 42 so that lever 33 and stop 42 move as a single unit.

Slot 45 is cut in stop 42 on a diagonal with respect to directions (A) and (B). Depression 45a is on the side toward direction (B), which loosens the cuff. It is cut one step deeper than the rest of the slot. Button shaft 40 goes through slot 46, which allows it to protrude downward. Ratchet 48 is mounted to this protruding shaft 40 in such a way that it is free to rotate. Detent 41 prevents ratchet 48 from coming loose. Ratchet 48 has two pawls 49 and two projections 50, 51 on its upper surface. Projection 50 fits into slot 45 as a guide. When the cuff is loosened, it is on the side of the slot closer to direction (A). The other projection, 51, contacts the bottom of stop 42 when the cuff is loosened. These projections are provided in order to insure that ratchet 48 can rotate smoothly.

Figure 2A:
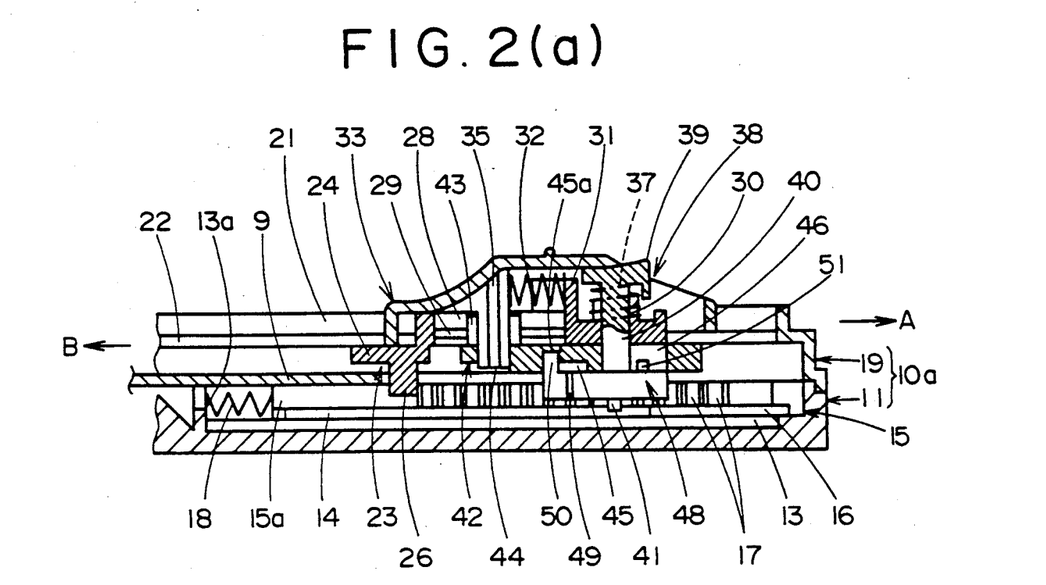
FIG. 2(a) cross sectional view of the cuff tightening unit of FIG. 1(a), shown with the cuff tightened.
Figure 2B:
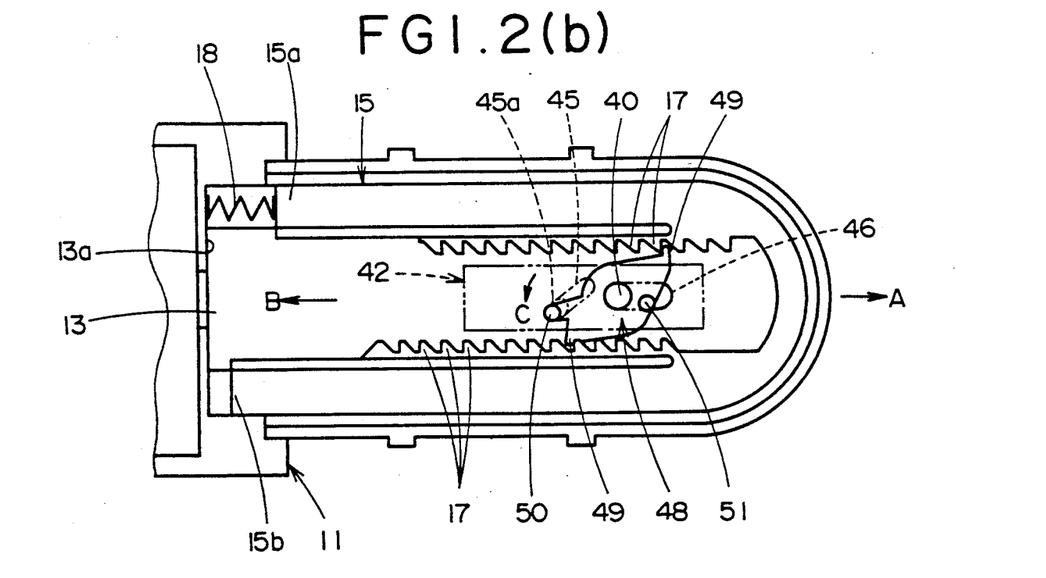
FIG. 2(b) shows the cuff tightening unit of FIG. 1(a), illustrating the relationship between the ratchet and cam when the cuff is tightened.
Figure 3A:
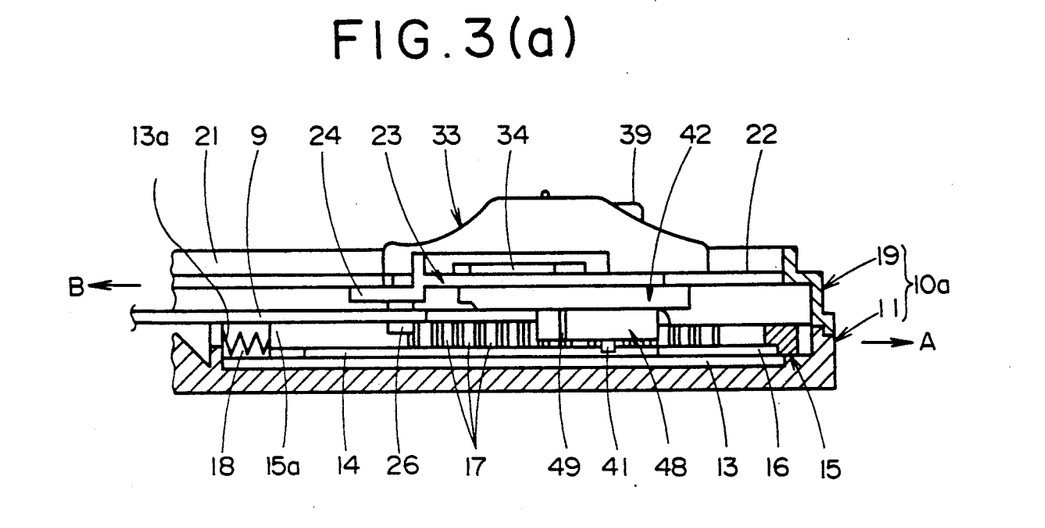
FIG. 3(a) is a cross sectional view of the cuff tightening unit of FIG. 1(a) when the tightening of the cuff has been completed.
Figure 3B:
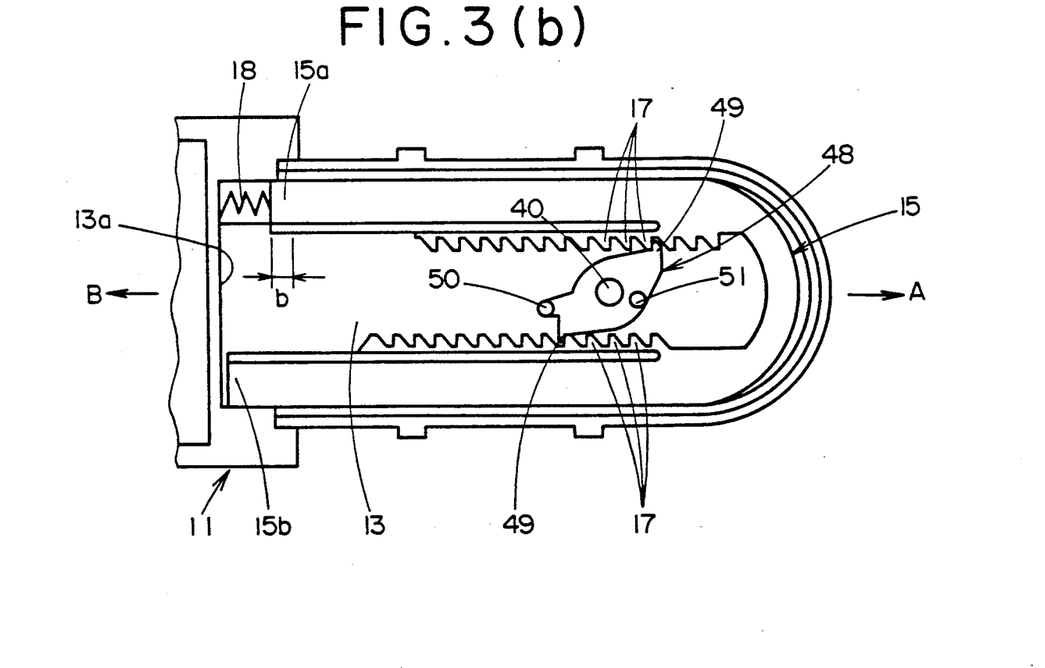
FIG. 3(b) shows the cuff tightening unit of FIG. 1(a), illustrating the relationship between the ratchet and cam when the tightening of the cuff has been completed.

The following is an explanation of the cuff tightening operation in the embodiment with reference to FIGS. 2 and 3. When force is applied to lever 33 in direction (A), which tightens the cuff, this force is transmitted to lever mounting 23 through coil spring 32, and lever mounting 23 begins to slide in direction (A). The protruding end 9 of the cuff is pulled in direction (A), and the cuff is tightened around the finger.

When the cuff is tightened, coil spring 32 is deformed by compression, and lever 33 and stop 42 slide against lever mounting 23 in direction (A). At this time the center of rotation of ratchet 48, i.e., button shaft 40, is anchored to the top surface of lever mounting 23, so projection 50 is guided by slot 45, and ratchet 48 rotates in direction (C).

When the value for the cuff tightening force is exceeded, pawls 49 on ratchet 48 engage in interdental spaces 17 can be seen in FIGS. 2(a) and (b). At the same time, projection 50 is pulled into depression 45a, projection 51 is pulled into slot 46, and ratchet 48 is secured by stop 42. When pawls 49 engage interdental spaces 17, lever mounting 23 is immobilized with respect to cam 15, and the cuff cannot be tightened any further.

When the operator's hand is removed from lever 33, air begins to enter the rubber chamber on the cuff, and cam 15 slides distance b in direction (B), the direction which loosens the cuff, while lever mounting 23 remains immobilized. This can be seen in FIGS. 3(a) and (b). This causes the cuff to loosen very slightly so the value for the tightening force of the cuff at the start of pressurization can be fixed at close to zero, and a correct blood pressure reading can be obtained. This distance b can be adjusted by varying the elasticity of coil spring 1B. Thus the movement of cam 15 can be controlled such that the cam does not move in direction (B) farther than is necessary.

To loosen the cuff, the operator pushes button head 39. When this button head is pushed, ratchet 48 moves downward, projections 50 and 51 are released from depression 45a and slot 46 respectively, and ratchet 48 becomes free to rotate. The force of coil spring 32 causes lever 33 and stop 42 to resume their former positions with respect to lever mounting 23. Ratchet 48 rotates in the direction opposite C, and pawls 49 disengage from interdental spaces 17. Lever mounting 23 can then slide in direction (B), and the cuff can be loosened. The force of coil spring 18 causes cam 15 to resume its former position.

In the embodiment described above, coil spring 18 is used to control the travel of cam 15. This structure acts to regulate rachet travel by permitting the rachet to travel either in direction (A) or in direction (B) while regulating the distance in either direction through which the rachet is permitted to travel. However, the invention is not limited to the use of such a coil spring. Any appropriate design modification can be made.

Another embodiment of this invention is explained below with reference to FIGS. 7 through 11. FIG. 11 is a frontal view of finger cuff-type electronic blood pressure monitor 101, in which the ratcheting device of this second embodiment is employed. The end of case 102 of this blood pressure monitor is formed into finger insertion unit 102a, within which a cuff with an air chamber [not pictured] identical to those of previous versions is provided. Case 102 has a slot 102b on it, in which the wrapping device for the cuff is located.

Figure 7A:
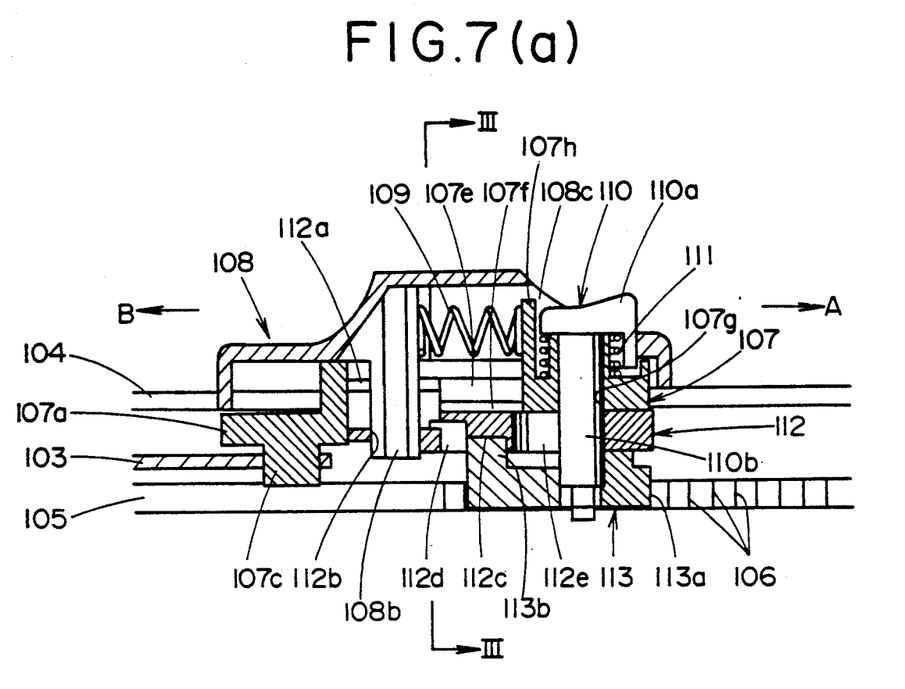
FIGS. 7(a) and (b) show, respectively, a cross sectional view of the cuff wrapping mechanism for the blood pressure monitor relating to a second embodiment of this invention, and a view of the mechanism of FIG. 7(a) as seen from the inside of the case.
Figure 7B:
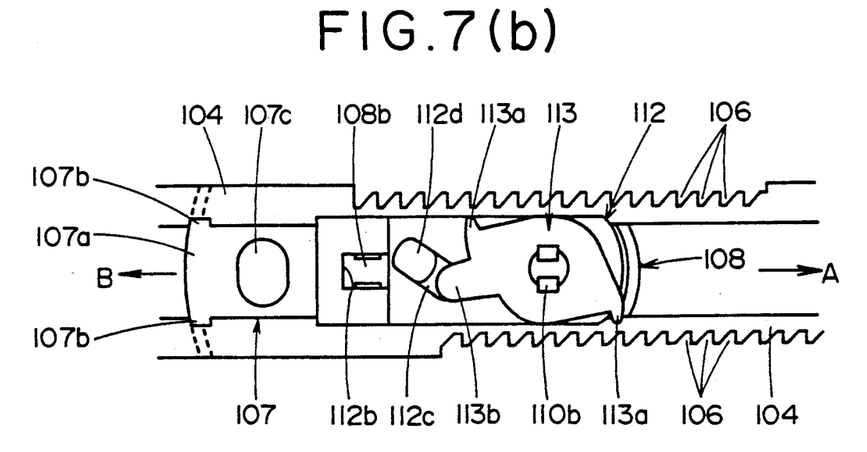
Figure 9:
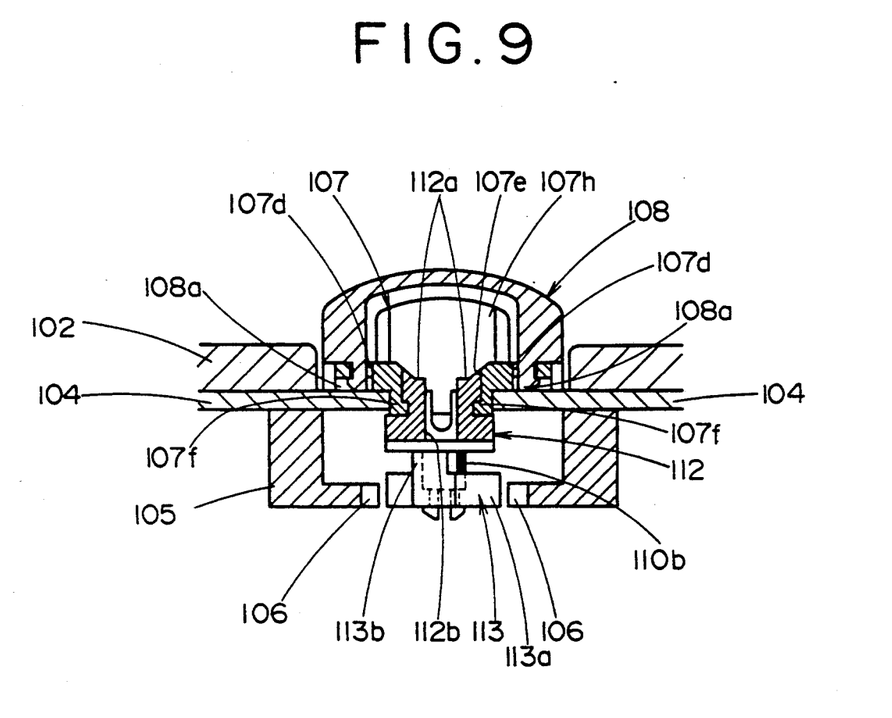
FIG. 9 is an enlarged view of the cross section taken along line III—III in FIG. 7(a).
Figure 10:
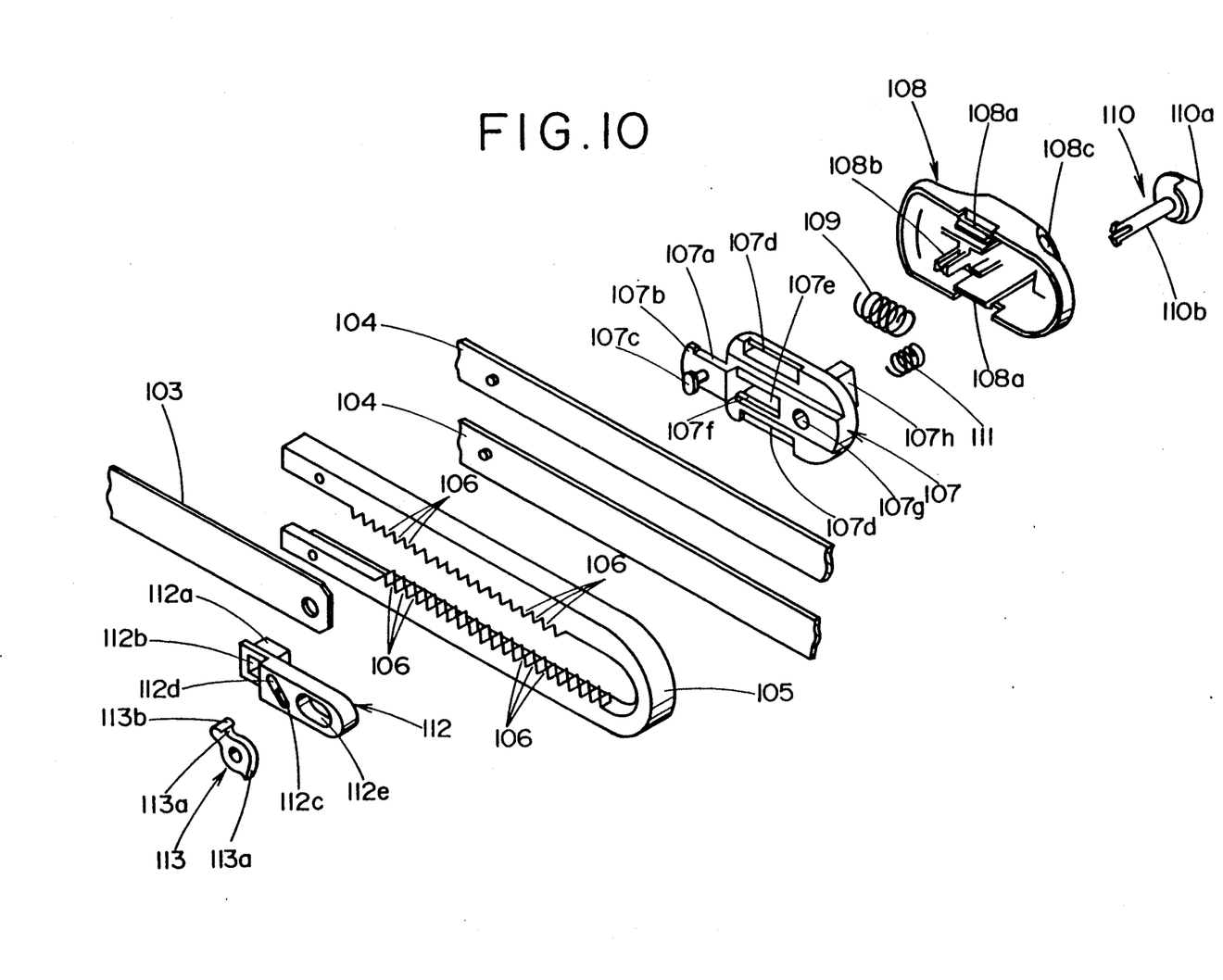
FIG. 10 shows an oblique exploded view of the disassembled parts of the cuff winding mechanism used in the blood pressure monitor of FIG. 7(a).
Figure 11:
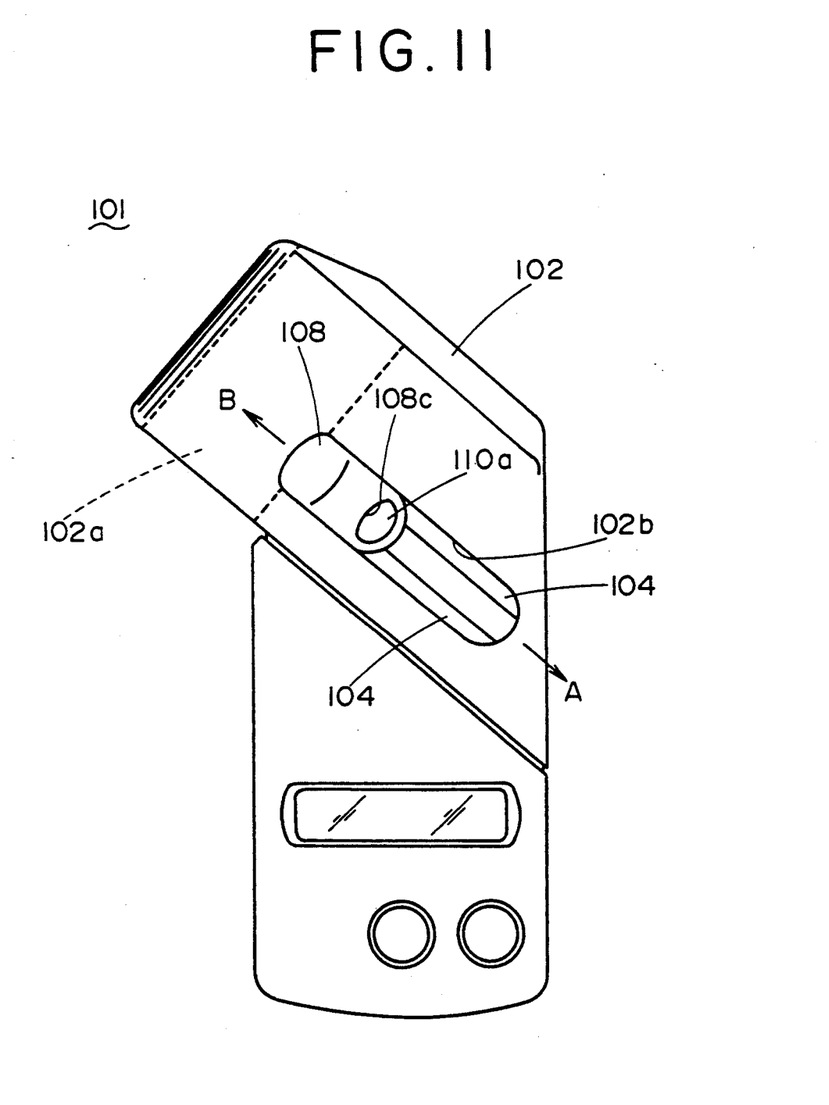
FIG. 11 is a frontal view of the finger cuff-type electronic blood pressure monitor in which the cuff winding mechanism of FIG. 7(a) is employed.

The wrapping device for the cuff, as shown in FIG. 10, includes button 110, lever 108, coil springs 109 and 111, lever mounting 107, cover 104, cam 105, stop 112 and ratchet 113. Cover 104 is fastened to the inner surface of case 102 and projects from slot 102b as shown in FIGS. 7, 9 and 11. Cam 105 is inside case 102, and is attached to the inner surface of cover 104. Cam 105 has sawteeth on either side of slot 102b extending along its length. The sawteeth are positioned beneath cover 104 but do not come in contact with it.

Lever mounting 107 is retained in slot 102b on the exterior of case 102. It can slide on cover 104 in either direction (A), which tightens the cuff, or direction (B), which loosens the cuff. The end portion 107a of lever mounting 107 depends within the case between the two portions of cover 104. Projections 107b prevent the lever mounting from coming loose. Anchor pin 107c depends from the end 107a of the lever mounting and secures the protruding end 103 of the cuff as shown in FIGS. 7(a) and 10. Lever 108 is mounted on lever mounting 107 in such a way that it can slide on the mounting in direction (A), which tightens the cuff, or in direction (B), which loosens the cuff. Tabs 108a on lever 108 engage in respective slots 107d on lever mounting 107. They serve to guide lever 108 in directions (A) and (B). Pin 108b depends from lever 108, passes through guide slot 107e on lever mounting 107, and protrudes downward. Coil spring 109 is interposed between lug 107h and the lower end of pin 108.

Button 110 is mounted on lever mounting 107. The shaft of this button, 110b, passes through hole 107g on lever mounting 107 and protrudes downward. Lever 108 has an opening 108c on it, so that the top 110b of the button will not contact the lever. Coil spring 111 is attached to button shaft 110b. It provides a force to move button 110 upward.

Stop 112 is mounted to the bottom surface of lever 107 in such a way that it allows the lever to slide in directions (A) and (B) against the lever mounting. Stop 112 has two tabs 112a on it. These tabs insert into guide slot 107e on the lever mounting and engage, respectively, with projections 107f. The lower end of pin 108b inserts into hole 112b so that lever 108 and stop 112 can move as a single unit against lever mounting 107.

Stop 112 has a slot 112c on it, which is oblique with reference to directions (A) and (B). On the side of this slot closer to direction (B), which loosens the cuff, there is a depression, 112d, which is one step deep. Hole 112e is for button shaft 110b. The button shaft passes through the hole and protrudes into the interior of the device. Ratchet 113 is mounted to this protruding button shaft 110b in such a way that it is free to rotate. Ratchet 113 has two pawls 113a and a projection 113b, which is higher than the rest of the ratchet. This projection 113b is guided by slot 112c. When no force is being applied to tighten the cuff, the projection will be on the end of slot 112c in the direction of direction (A).

Figure 8A:
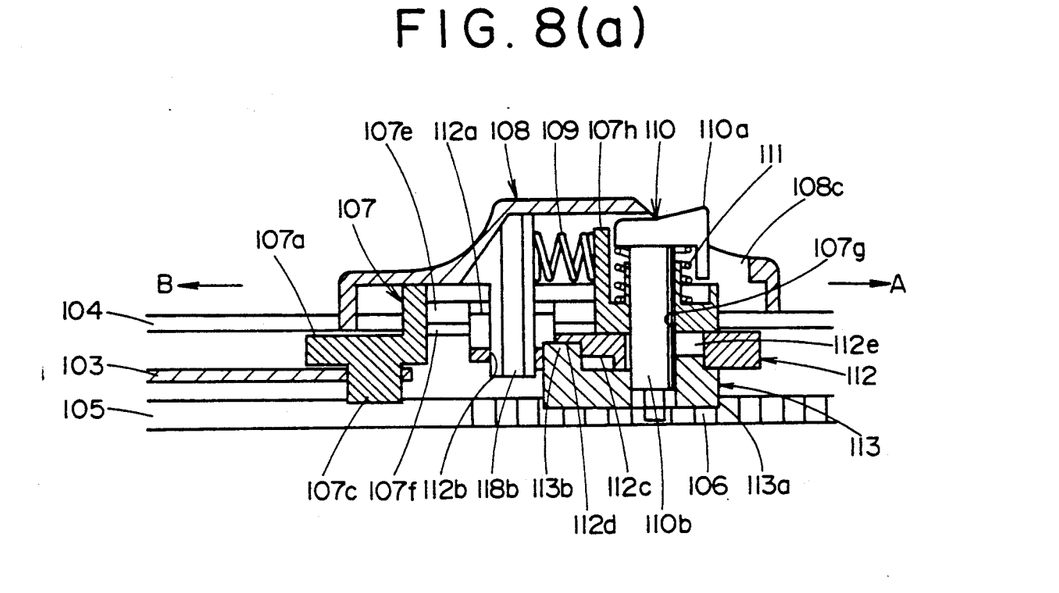
FIGS. 8(a) and (b) show respectively a cross sectional view of the cuff wrapping mechanism used in the blood pressure monitor of FIG. 7(a), with the cuff tightened, and the view as seen from the inside of the case.
Figure 8B:
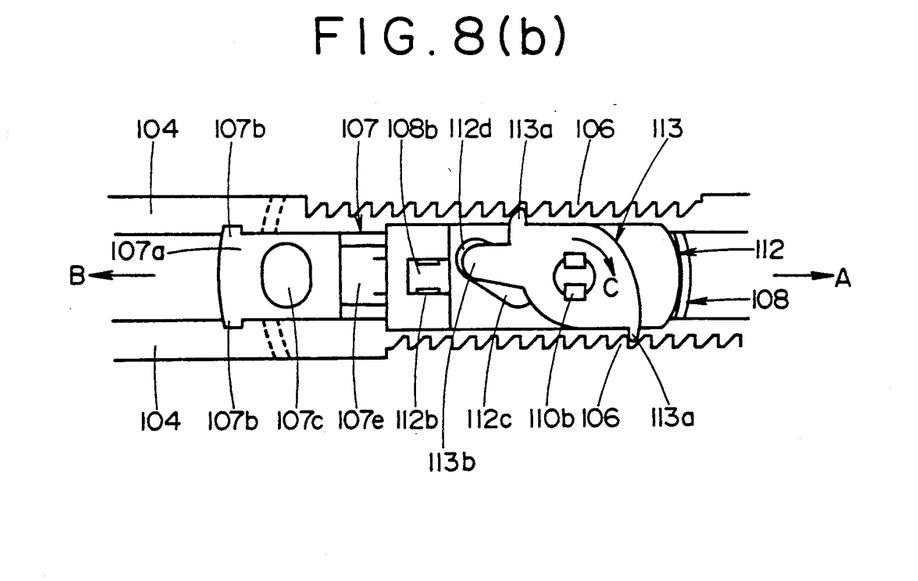

We shall next explain the operation of the cuff wrapping mechanism in this second embodiment, with reference to FIGS. 8(a) and (b). When force is applied to lever 108 in direction (A), which tightens the cuff, this force is transmitted to lever mounting 107 through coil spring 109, and lever mounting 107 begins to slide in direction (A). The protruding end 103 of the cuff is pulled in direction (A), and the cuff is wrapped around the finger.

When the cuff is wrapped around the finger, coil spring 109 is compressively deformed, and lever 108 and stop 112 slide against lever mounting 107 in direction (A), which tightens the cuff. Because the center of rotation of rachet 113 is fixed to lever mounting 107, projection 113b is guided by slot 112c, and ratchet 113 rotates in direction C.

When the tightening force exceeds a given value, pawls 113a on ratchet 113 engage respective interdental spaces 106. At the same time, projection 113b engages in slot 112c, and ratchet 113 is fixed in that position. When pawls 113a engage interdental spaces 106, lever mounting 107 is arrested in its position at that moment, and the cuff cannot be tightened or loosened any further. Because pawls 113a and interdental spaces 106 do not come in contact until lever mounting 107 is arrested, the force used to tighten the cuff is not variable as in former designs. As a result, there is less chance of overtightening the cuff, and operating noise is kept to a minimum.

When the measurement of blood pressure has been completed, the operator pushes button head 110b, and the entire ratchet 113 is moved downward toward the interior of the device. When ratchet 113 moves downward, projection 113b disengages from slot 112c, and the ratchet becomes free to rotate in the opposing direction. Consequently, pawls 113a disengage from interdental spaces 106, and lever mounting 107 moves in direction (B), enabling the cuff to be loosened.

Although the invention has been described with respect to two embodiments depicted in this application, persons skilled in this art will readily recognize and be able to practice other equivalent embodiments of the invention upon consideration of the specification, claims and drawings of this application.

What is claimed is:

1. A ratcheting device for use in tightening the cuff of a blood pressure monitor, comprising:
   a lever;
   lever mounting means for mounting the lever so that the lever can be moved in a given direction or a direction opposite the given direction;
   an elastic body disposed between the lever and the lever mounting means so as to transmit a force applied to the lever into the lever mounting means by elastic deformation of the elastic body;
   interdental spaces between saw teeth provided on an inner surface of a cam, the interdental spaces extending in the given and opposite directions in which the lever moves;
   a ratchet provided with pawls thereon which can engage with the interdental spaces; and
   immobilizing means for immobilizing the ratchet so that the pawls engage in the interdental spaces when a pressure applied to the lever exceeds a given value.

2. The ratcheting device of claim 1,
   wherein the ratchet is mounted on a shaft on the lever mounting means so that it can rotate about the shaft and engage in the interdental spaces; and
   the immobilizing means comprises guiding means for guiding the ratchet when it rotates and engages in the interdental spaces, thus immobilizing itself in response to the pressure in excess of a given value being applied to the lever.

3. The ratcheting device of claim 2, wherein the lever mounting means is adapted to receive an end of a cuff of a blood pressure monitor.

4. The ratcheting device of claim 1, further comprising regulating means for permitting the rachet to travel either in the given direction or the opposite direction and for regulating the distance in the given or opposite direction through which the rachet is permitted to travel.

5. The ratcheting device of claim 4, wherein the lever mounting means is adapted to receive an end of a cuff of a blood pressure monitor.

6. The ratcheting device of claim 1, wherein the lever mounting means is adapted to receive an end of a cuff of a blood pressure monitor.

* * * * *